United States Patent [19]
Clinton et al.

[11] Patent Number: 5,295,970
[45] Date of Patent: Mar. 22, 1994

[54] APPARATUS AND METHOD FOR VASCULAR GUIDE WIRE INSERTION WITH BLOOD FLASHBACK CONTAINMENT FEATURES

[75] Inventors: Mary B. Clinton, Pearl River, N.Y.; Frederick C. Houghton, Sussex; Joseph J. Gregg, Hasbrouck Heights, both of N.J.

[73] Assignee: Becton, Dickinson and Company, Franklin Lakes, N.J.

[21] Appl. No.: 14,036

[22] Filed: Feb. 5, 1993

[51] Int. Cl.⁵ ............................................... A61M 5/00
[52] U.S. Cl. ..................................... 604/168; 604/167
[58] Field of Search ...................... 604/168, 167, 900

[56] References Cited
U.S. PATENT DOCUMENTS

| | | | |
|---|---|---|---|
| 4,020,835 | 5/1977 | Nordstrom et al. | 604/168 |
| 4,193,399 | 3/1980 | Robinson | 604/168 |
| 4,904,240 | 2/1990 | Hoover | 604/168 |
| 5,032,116 | 7/1991 | Peterson et al. | 604/168 |
| 5,066,284 | 11/1991 | Mersch | 604/168 |
| 5,098,395 | 3/1992 | Fields | 604/168 |
| 5,108,375 | 4/1992 | Harrison et al. | 604/167 |
| 5,120,319 | 6/1992 | Van Heugten et al. | 604/168 |
| 5,242,414 | 9/1993 | Kischell et al. | 604/168 |

Primary Examiner—Paul J. Hirsch
Attorney, Agent, or Firm—John L. Voellmicke

[57] ABSTRACT

Apparatus and method are provided for containing blood flashback during insertion of a guide wire into a blood vessel. The apparatus includes a barrel having a flashback chamber. An inner cannula in the flashback chamber communicates with an inserter needle mounted on the barrel. The inner cannula includes an aperture communicating with the flashback chamber. A porous vent plug is slidably disposed in the chamber in fluid-tight engagement with both the barrel and the inner cannula. The vent plug can be slid from a proximal position where the aperture in the inner cannula is exposed to a distal position where the aperture in the inner cannula is blocked. A guide wire in the inner cannula blocks blood flow. The vent plug and the guide wire are retained proximally of the aperture in the inner cannula until blood flashback is observed. The vent plug is then axially advanced to cover the aperture and stop further blood flow. The guide wire can then be advanced safely into the blood vessel.

26 Claims, 10 Drawing Sheets

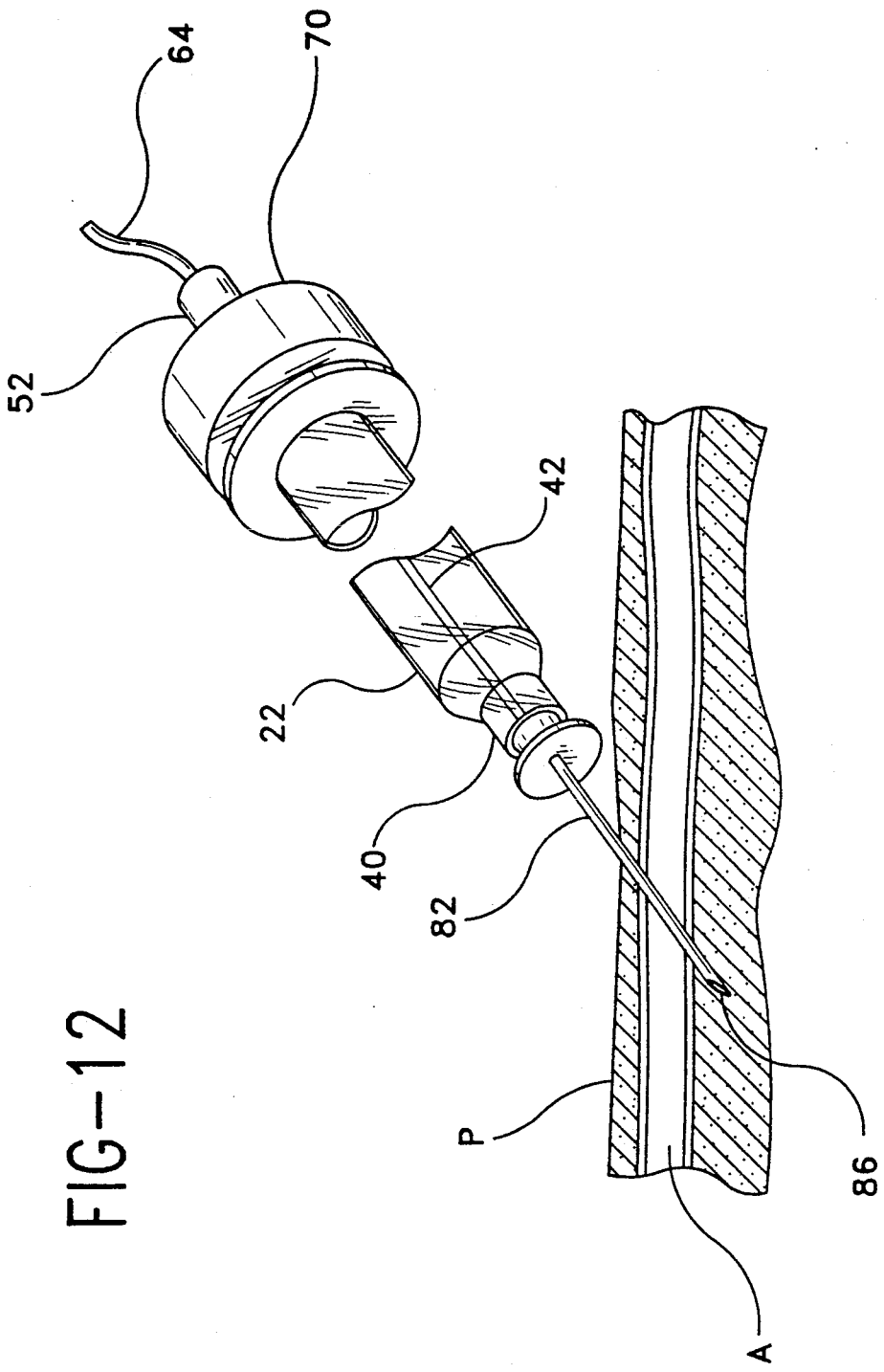

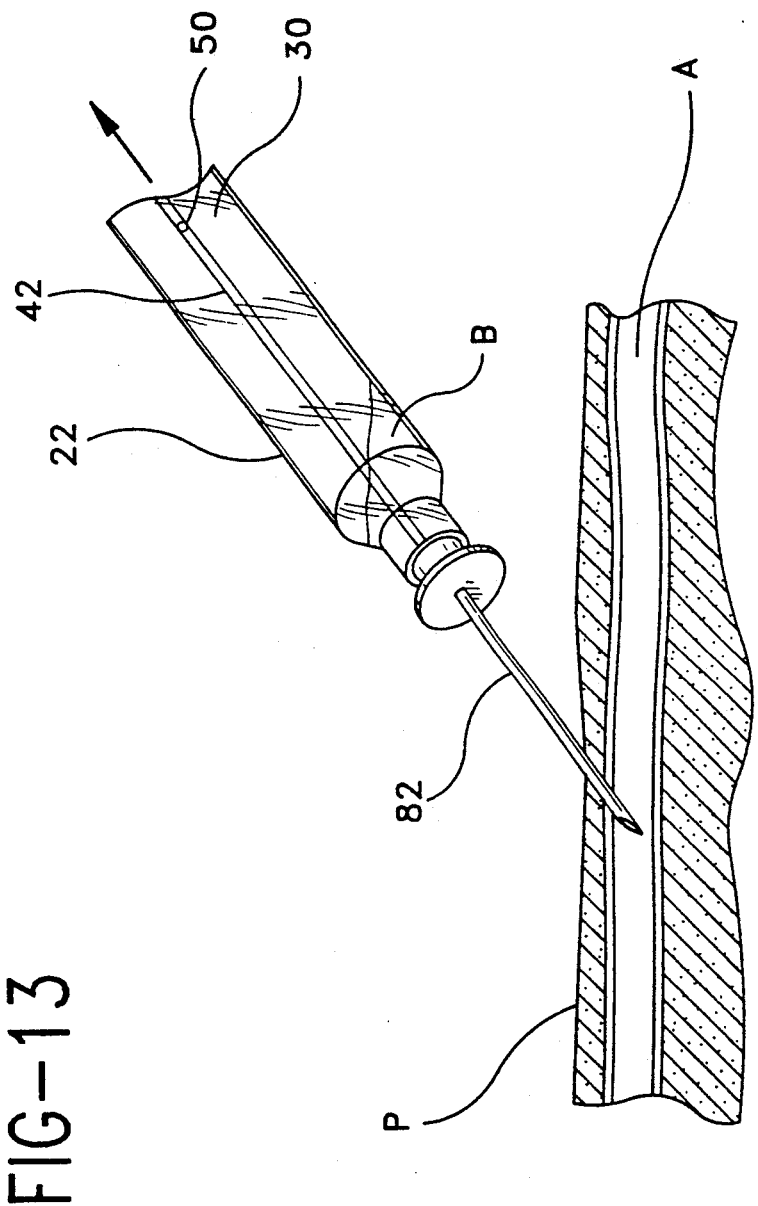

APPARATUS AND METHOD FOR VASCULAR GUIDE WIRE INSERTION WITH BLOOD FLASHBACK CONTAINMENT FEATURES

FIELD OF THE INVENTION

The present invention relates to an apparatus for safely containing blood flashback that is generated during procedures for inserting a guide wire or catheter into a blood vessel.

DESCRIPTION OF THE PRIOR ART

Cardiological and radiological procedures often require a guide wire and/or a catheter to be inserted into and advanced longitudinally through a blood vessel. Prior art apparatus for such procedures utilize an inserter needle with open proximal and distal ends. The cardiologist or radiologist advances the distal end of the inserter needle into the blood vessel. Entry into a blood vessel is verified by blood flashback from the proximal end of the inserter needle. The type of blood vessel that has been accessed generally can be determined by characteristics of the blood flashback. Access to an artery is characterized by spurting or spraying of the pulsating arterial blood from the open proximal end of the inserter needle. Access to a vein is characterized by a more uniform flow of blood. The cardiologist or radiologist using the prior art apparatus then urges the guide wire through the inserter needle and into the blood vessel.

Some cardiologists or radiologists prefer a double wall puncture technique to access a blood vessel. With this technique a solid stylet is slid into the inserter needle. The assembled inserter needle and stylet are urged into the blood vessel and out the opposed side of the blood vessel. The stylet is then slidably withdrawn from the inserter needle and the inserter needle is pulled back sufficiently for the open distal end to re-enter the blood vessel. As with the simpler single wall technique, the presence of the open distal end of the inserter needle in the blood vessel is verified by blood flow from the proximal end of the inserter needle.

The above described prior art apparatus and process for insertion of an arterial guide wire or catheter is simple and effective and has been widely employed. However, the spurting of arterial blood inherent with the above described prior art apparatus has become a major concern. Blood that spurts from the proximal end of the needle cannula after the distal end enters the artery can contact eyes, lips and skin of the cardiologist or radiologist trying to access the blood vessel. As a result, health care workers have gone to elaborate extremes to avoid blood contact, including wearing protective gloves, masks and goggles.

A prior art device to contain blood flashback during cannulating procedures is shown in U.S. Pat. No. 5,108,375. The device shown in U.S. Pat. No. 5,108,375 includes a needle cannula mounted to a hub. The hub of the needle cannula is mounted to a large heart-shaped reservoir for receiving pulsating blood from the artery accessed by the needle cannula. A tubular wire guide passes through the reservoir and has a distal end that can be urged into communication with the proximal end of the needle cannula. The proximal end of the tubular wire guide is provided with a resilient one-way hemostatic valve, such as a resilient self-sealing membrane. A catheter guide wire can be passed through the resilient one-way hemostatic valve at the proximal end of the tubular wire guide, and can be fed entirely through the wire guide and needle cannula, and into the artery. The device of U.S. Pat. No. 5,108,375 appears to require a very large reservoir in order to prevent a rapid rise of air pressure to levels that would impede the in-flow of blood. However, the larger reservoir makes this device very cumbersome to handle and store.

Another prior art apparatus that attempts to contain blood flashback during arterial cannulation includes a Y-site with an outlet leg, a guide wire inserting leg linearly aligned to the outlet leg and a side-arm aligned to the guide wire inserting leg at an acute angle. A valve is mounted to the guide wire inserting leg. A plastic sheath is mounted over the side arm and is intended to receive the blood flashback. The flexible nature of the plastic sheath on this apparatus can lead to rupture or accidental puncture by sharp instruments used nearby. Additionally, this apparatus requires the complication of properly manipulating the valve on the guide wire inserting leg to enable insertion of the guide wire and to prevent leakage of blood.

The prior art also includes vascular access means and blood collection devices which employ porous plugs. A porous plug may be formed from an open pore plastic having a pore size in the range of 10-15 microns to provide a flow path for venting air, but to prevent the transmission of fluid, such as blood, therethrough. A prior art device employing a porous plug is shown, for example, in U.S. Pat. No. 4,193,399. The apparatus shown in U.S. Pat. No. 4,193,399 includes a small chamber for receiving blood flashback. The chamber communicates with a needle cannula for accessing a blood vessel. A solid porous plug is disposed at the proximal end of the chamber to permit air in the chamber to escape as the chamber fills up with blood. The apparatus shown in U.S. Pat. No. 4,193,399 has no means for introducing a guide wire, without first removing the porous plug, and thereby permitting the health care worker to be exposed to the collected blood in the chamber. Also, the porous plug must be removed to determine if the needle is in a vein or an artery.

SUMMARY OF THE INVENTION

The subject invention is directed to apparatus for safely inserting a guide wire into a blood vessel. More particularly, the apparatus of the subject invention enables efficient containment of blood flashback that is required to verify entry to a blood vessel.

The apparatus of the subject invention comprises an elongate barrel having an open proximal end, an opposed distal end and a chamber wall extending therebetween. The chamber wall defines a fluid flashback chamber extending into the proximal end of the barrel. The chamber wall is transparent to enable the user of the apparatus to observe blood flow into the chamber, as explained herein, for determining when a blood vessel has been accessed, and to distinguish arterial blood flow from venous blood flow. The distal end of the barrel includes a passage extending therethrough and communicating with the chamber in the barrel. The distal end of the barrel further includes means for mounting an inserter needle thereto, such that the lumen of the inserter needle communicates with the passage and the chamber of the barrel.

An inner cannula is centrally mounted in the chamber of the barrel and extends substantially the entire length thereof. The inner cannula includes opposed proximal and distal ends and a lumen extending therebetween. The distal end of the inner cannula is securely mounted in the tip of the barrel to communicate with the passage through the tip. The proximal end of the inner cannula may extend to or beyond the proximal end of the barrel. The inner cannula preferably is formed from a transparent material to enable observation of blood flow therein.

The inner cannula is provided with at least one aperture extending therethrough at a location between the proximal and distal ends. The aperture extends through a portion of the inner cannula disposed within the barrel, and preferably through a portion of the inner cannula closer to the proximal end of the barrel.

A stopper may be mounted over the proximal end of the inner cannula. The stopper includes a guide wire passage extending therethrough and communicating with the lumen of the inner cannula. The proximal end of the stopper may be flared to facilitate insertion of a guide wire into the guide wire passage and toward the lumen of the inner cannula. The proximal end of the stopper may further include guide wire holding means for retaining a portion of the guide wire. Preferably, the guide wire holding means comprises a slit at the proximal end of the stopper for retaining the guide wire. The holding means may be used to releasably retain a portion of a guide wire, adjacent an end of the guide wire, while the blood vessel is being accessed by the inserter needle. Upon entry of the inserter needle into the blood vessel, the guide wire may be released from the holding means of the stopper and advanced longitudinally through the inner cannula, through the inserter needle and into the accessed blood vessel.

The guide wire used with the subject apparatus preferably defines an outside diameter approximately equal to the inside diameter of the lumen through the inner cannula and/or the inside diameter of the passage through the stopper. Thus, the guide wire helps prevent the flow of blood completely through the inner cannula and from the proximal end of the apparatus.

The apparatus of the subject invention further includes a porous vent plug securely engaged in the proximal end of the barrel. The porous vent plug is formed from a material that transmits gas, but that prevents flow of liquids, such as blood. The porous vent plug, in the preferred embodiment, defines an outer surface configured and dimensioned for sliding fluid-tight engagement with the chamber wall of the barrel to prevent escape of blood between the porous vent plug and the barrel. The porous vent plug further includes a central aperture extending longitudinally therethrough. The central aperture is in sliding fluid-tight engagement around the inner cannula. The vent plug may be slid axially relative to both the barrel and the inner cannula from a proximal position to a distal position. The distal end of the vent plug is disposed proximal of the aperture through the inner cannula when the vent plug is in its proximal position. However, the vent plug sealingly blocks the aperture through the inner cannula when the vent plug is slid to its distal position in the barrel. Thus, the vent plug can alternately open or sealingly close the aperture through the inner cannula.

The apparatus of the preferred embodiment is employed with the vent plug initially in its proximal position in the barrel, such that the aperture through the inner cannula is open to enable fluid communication between the chamber and the lumen of the inner cannula. A guide wire is mounted in the proximal end of the inner cannula such that the end of the guide wire is disposed proximally of the aperture through the inner cannula. The guide wire may be retained in this initial position by holding means in the stopper. As noted above, the outside diameter of the guide wire is approximately equal to the inside diameter defined by the lumen of the inner cannula and/or the passage through the stopper. Thus, the guide wire prevents blood flow completely through the inner cannula and from the proximal end of the apparatus.

The radiologist or cardiologist uses the apparatus by urging the distal end of the inserter needle into the patient. Upon accessing a blood vessel with the inserter needle, blood will flow through the inserter needle, through the lumen of the inner cannula, through the aperture in the inner cannula and into the flashback chamber of the barrel. This flow of blood can be readily observed through the transparent chamber wall and through the inner cannula, if it is made of transparent material. Additionally, the proximal position of the aperture through the inner cannula enables the cardiologist or radiologist to observe the characteristics of the blood flow, and to distinguish a pulsating arterial blood flow from a slower venous blood flow. Once the cardiologist or radiologist is confident that the distal tip of the needle cannula is in an appropriate blood vessel, the cardiologist may then disengage the guide wire from the holding means and advance the guide wire catheter distally through the inner cannula and the inserter needle and into the artery of the patient. Once the guide wire catheter is fed sufficiently into the appropriate artery, the vent plug may be advanced to its distal position within the barrel to cover the aperture through the inner cannula. The vent plug thus serves to prevent further flows of blood into the chamber, while the guide wire functions to prevent escape of blood from the proximal end of the inner cannula. Remaining portions of the apparatus may then be withdrawn proximally and separated from the guide wire.

BRIEF DESCRIPTION OF THE DRAWINGS

FIG. 12 is a cross-sectional view similar to FIGS. 10 and 11, but showing a third operational condition of the alternate embodiment.

FIG. 13 is a cross-sectional view similar to FIGS. 10-12, and showing a fourth operational condition of the alternate embodiment.

DETAILED DESCRIPTION OF THE PREFERRED EMBODIMENT

Figure 1:
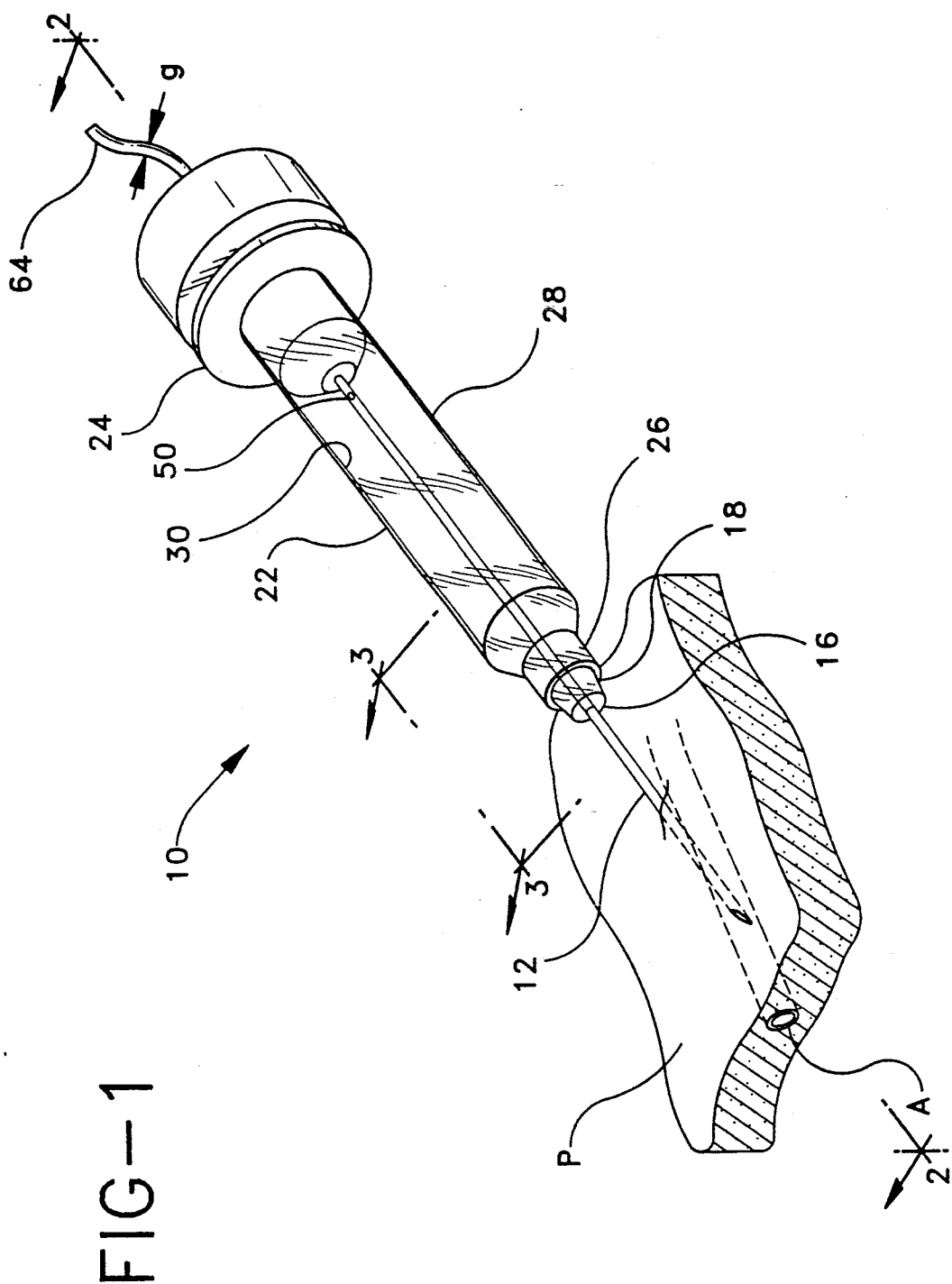
FIG. 1 is a perspective view of a blood flashback containment apparatus in accordance with the subject invention inserted in a patient.
Figure 2:
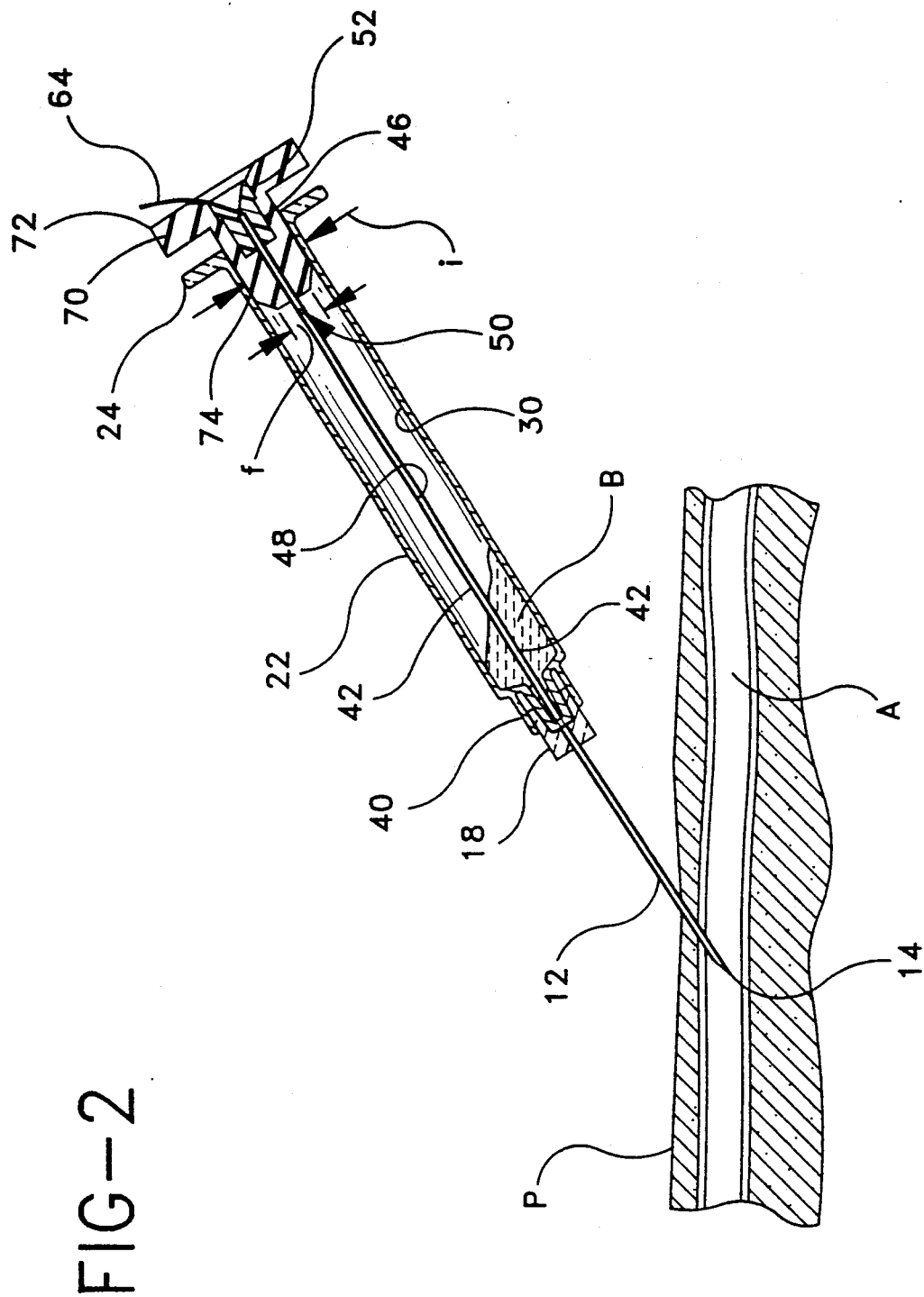
FIG. 2 is a cross-sectional view taken along line 2—2 in FIG. 1.
Figure 3:
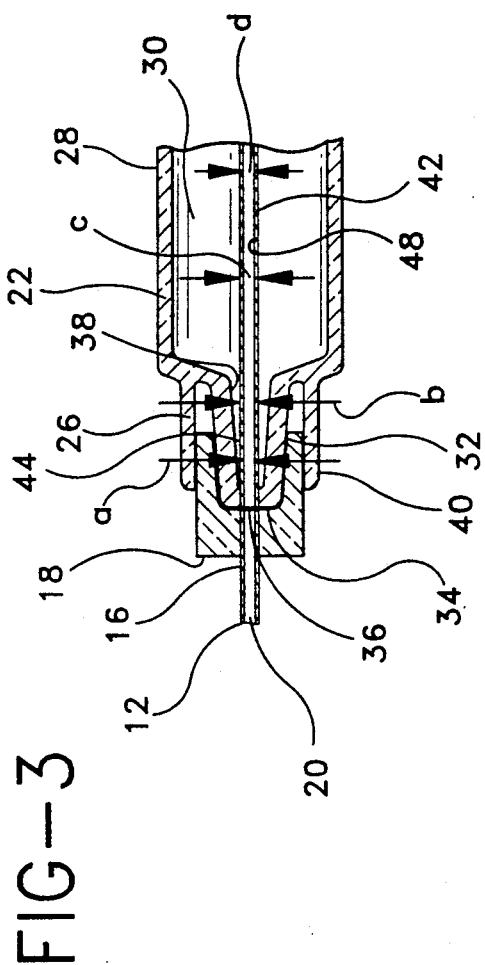
FIG. 3 is an enlarged cross-sectional view taken along line 3—3 in FIG. 1.

A blood flashback containment apparatus in accordance with the subject invention is identified generally by the numeral 10 in FIGS. 1-3 and 7-9. Apparatus 10 includes an elongate inserter needle 12 having a pointed distal end 14 for entry into a blood vessel A of a patient P. Inserter needle 12 further includes a proximal end 16 mounted to a needle hub 18. A lumen 20 extends longitudinally through inserter needle 12 as shown in FIGS. 2 and 3.

Apparatus 10 further includes an elongate cylindrical barrel 22 formed from a transparent thermoplastic material. Barrel 22 includes an open proximal end 24, a distal end 26 and a cylindrical chamber wall 28 extending therebetween. A blood flashback chamber 30 is defined within cylindrical chamber wall 28 and extends substantially from proximal end 24 to distal end 26.

Distal end 26 of barrel 22 includes an elongate axially aligned tip 32 which terminates at a radially aligned distal end wall 34 having a distal opening 36 of diameter "a" extending therethrough. Elongate tip 32 includes a passage 38 extending therethrough and providing communication between distal opening 36 and blood flashback chamber 30. Passage 38 defines an inside diameter "b" adjacent distal end wall 34.

A luer collar 40 also is disposed at distal end 26 of barrel 22 in spaced concentric relationships around tip 32. Luer collar 40 includes an array of internal threads for threadedly engaging needle hub 18. As shown most clearly in FIG. 3, needle hub 18 is threadedly engaged with luer collar 40 to provide fluid communication between lumen 20 of inserter needle 12 and distal opening 36 in distal end wall 34 of tip 32.

Apparatus 10 further includes an inner cannula 42 securely mounted in barrel 22. More particularly, inner cannula 42 includes a distal end 44, a proximal end 46 and a lumen 48 extending therebetween. Inner cannula 42 defines an outside diameter "c" approximately equal to inside diameter "b" of passage 38 adjacent distal end wall 34. Additionally, lumen 48 of inner cannula 42 defines an inside diameter "d" which is approximately equal to inside diameter "a" of distal opening 36 through distal end wall 34 of barrel 22. As shown most clearly in FIG. 3, distal end 44 of inner cannula 42 is securely mounted in tip 32 and adjacent distal end wall 34 thereof. Thus, lumen 48 of inner cannula 42 is in fluid communication with distal opening 36 through distal end wall 34 and with lumen 20 of inserter needle 12. Inner cannula 42 preferably defines an axial length greater than the axial length of barrel 22. Thus, proximal end 46 of inner cannula 42 projects beyond proximal end 24 of barrel 22.

Inner cannula 42 is provided with a pair of apertures 50 spaced 180° from one another and extending through inner cannula 42 at an axial position within barrel 22. As explained further herein, apertures 50 enable blood flashback from inner cannula 42 to flow into chamber 30.

Figure 5:
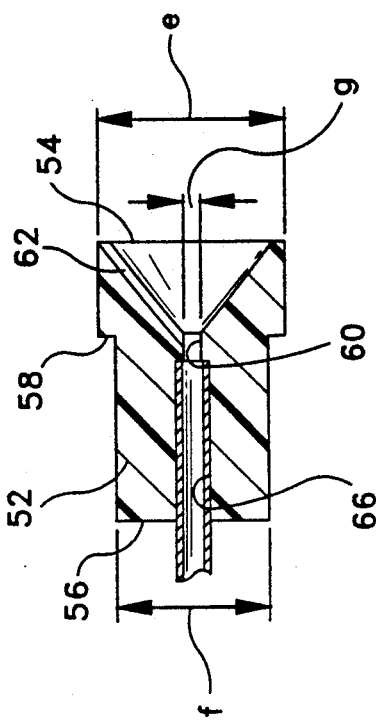
FIG. 5 is a cross-sectional view taken along line 5—5 in FIG. 4.
Figure 4:
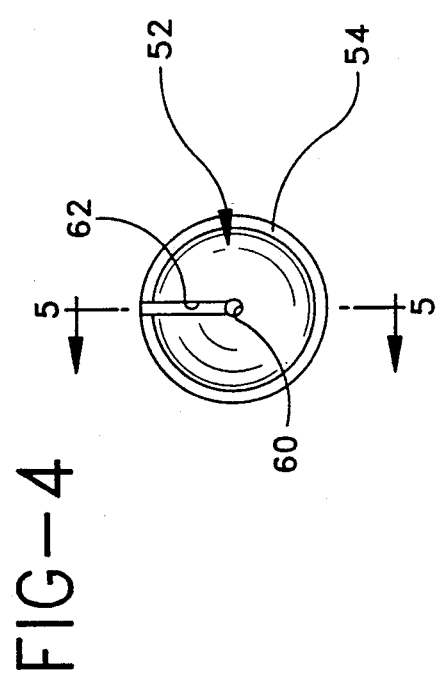
FIG. 4 is an elevational view of the proximal end of the stopper of the subject apparatus.
Figure 6:
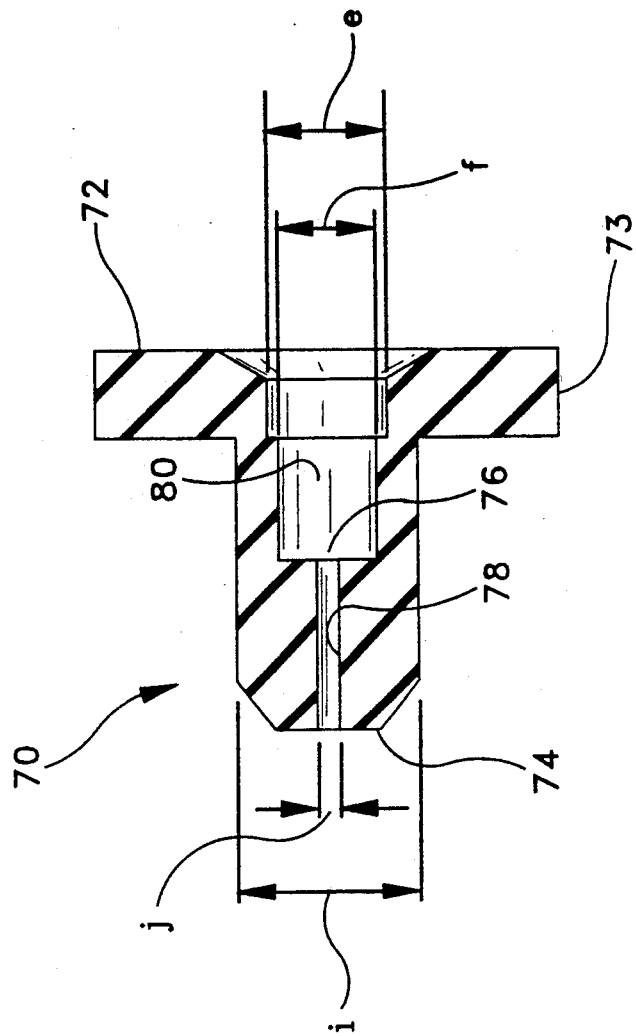
FIG. 6 is a cross-sectional view of the porous vent plug of the subject invention.

Apparatus 10 further includes a stopper 52 mounted to distal end 46 of inner cannula 42. As shown most clearly in FIGS. 4 and 5, stopper 52 is of generally stepped cylindrical configuration with a proximal end 54 defining a major external diameter "e" and a distal end 56 defining a minor external diameter "f". A generally radially aligned step 58 extends between the major and minor diameter portions at a location intermediate opposed proximal and distal ends 54 and 56 respectively.

Stopper 52 includes a guide wire aperture 60 extending axially into proximal end 54 of stopper 52. Portions of stopper 52 at the interface of proximal end 54 and guide wire aperture 60 are chamfered to define a flared entry into guide wire aperture 60. Proximal end 54 of stopper 52 further includes a slit 62 for engaging a guide wire 64 as explained further herein. Portions of guide wire aperture 60 disposed distally of the chamfer define an inside diameter "g" which is approximately equal to inside "d" of lumen 50 through inner cannula 42 and approximately equal to the outside diameter of guide wire 64.

Stopper 52 further includes an axially aligned cannula mounting aperture 66 extending into distal end 56 and into communication with guide wire aperture 60. However, cannula mounting aperture 66 at distal end 56 of stopper 52 defines an inside diameter "h" which is approximately equal to outside diameter "c" of inner cannula 42, and which therefore is greater than diameter "g" of guide wire aperture 60 in stopper 52. Thus, as shown most clearly in FIGS. 2 and 7-9, proximal end 46 of inner cannula 42 is securely retained in a fixed axial position within cannula mounting aperture 66 of stopper 52. The different diameters of aperture 66 and 60 prevent stopper 52 from shifting in a distal direction relative to inner cannula 42. Additionally, engagement of distal end 44 of inner cannula 42 adjacent distal wall 34 of tip 32 on barrel 22 prevents the assembled stopper 52 and inner cannula 42 from shifting distally in barrel 22.

Apparatus 10 further includes a vent plug 70 formed from a porous material, preferably plastic, which permits flow of gaseous material therethrough but which is substantially impervious to liquids. The porous vent plug is an important feature of the instant invention. By using a porous vent plug the entire volume of the barrel may be filled with blood because air is allowed to leave the chamber as blood enters the chamber. Without the porous vent plug air pressure will build up in the barrel to prevent its filling with blood and to compromise the ability to identify arterial blood flow. Without the porous vent plug the chamber would have to be many times larger in volume than is necessary with the porous vent plug. It should be noted that the porous vent plug serves two functions. It provides an air permeable, liquid impermeable barrier between the chamber and the exterior of the barrel for allowing air to leave the chamber as blood enters the chamber through the aperture in the inner cannula. The plug also serves the purpose of sealing the proximal end of the barrel to define the proximal end of the chamber. It is within the purview of the instant invention to include these functions being satisfied by separate elements. For example, the barrel may be provided with an aperture which is sealed by a plug or sheet of air permeable, liquid impermeable material which will allow air to leave the chamber as blood enters the chamber. The proximal end of the chamber can be sealed to the environment by a solid plug which is not air permeable or any other structure suitable for defining an enclosed chamber for collecting blood. The use of a porous vent plug which serves two functions is merely preferred and not intended to limit the scope of the invention.

Vent plug 70 includes opposed proximal and distal ends 72 and 74 respectively. Distal end 74 of vent plug 70 is of generally cylindrical shape with an outside diameter "i" approximately equal to the inside diameter of chamber 30 in barrel 22. Thus, distal portions of vent plug 70 can be disposed in sliding fluid-tight engagement within barrel 22. However, proximal end 72 of vent plug 70 defines a large diameter flange 73 which limits the amount of insertion of vent plug 70 into chamber 30 of barrel 22.

Vent plug 70 is characterized by a stepped aperture, identified generally by the numeral 76, which extends entirely through vent plug 70 from proximal end 72 to distal end 74. Stepped aperture 76 defines a small diameter portion 78 adjacent distal end 74 with an inside diameter "j" which is approximately equal to outside diameter "c" of inner cannula 42. Thus, as shown most clearly in FIGS. 7-9, inner cannula 42 may be disposed in sliding fluid-tight engagement relative to small diameter portion 78 of aperture 76 through vent plug 70. Aperture 76 of vent plug 70 further defines a stepped stopper seat 80 proximally of small diameter portion 78. Stopper seat 80 is configured to engage stopper 52 in sliding engagement which is preferably fluid-tight. The range of movement between stopper 52 and vent plug 70 is limited by the geometry and dimensions of the respective components as shown herein.

Apparatus 10 is assembled as shown in FIG. 2 with vent plug 70 slidably engaged in chamber 30 of barrel 22 adjacent proximal end 24 thereof. Proximal end 46 of inner cannula 42 is securely engaged in stopper 52. Distal end 44 of inner cannula 42 then is passed through vent plug 70, and is securely seated in passage 38 through tip 32 of barrel 22. In this seated position, stopper 52 will be disposed in fluidtight engagement within stopper seat 76 of vent plug 70. Additionally, portions of inner cannula 42 adjacent to stopper 52 are in sliding fluid-tight engagement within small diameter aperture 78 of vent plug 70.

In use, as will be explained in more detail, it is desirable to prevent blood from coming out of the device through the proximal end of the inner cannula. Means for preventing blood flow out of the proximal end of the inner cannula can include the guide wire being dimensioned and disposed within the inner cannula so that the blood, under arterial blood pressure, cannot flow around through the space between the outside of the guide' wire and the inside of the inner cannula. The means for preventing blood flow out of the proximal end o the inner cannula can also include dimensioning the stopper, such as stopper 52 to have an aperture 60 which is smaller in diameter than the guide wire so that when the guide wire's present blood cannot flow out of the proximal end of the device. Means for preventing blood flow out of the proximal end of the inner cannula can also include a valve attached to the proximal end of the device which can be shut to prevent blood flow. The known Tuohy Borst adapter can be used to block the flow of blood and also to hold the guide wire in the selected axial position with respect to the device.

As shown in FIG. 2, vent plug 70 is slidably moved to its proximal position, such that apertures 50 through inner cannula 42 are exposed. Needle hub 18 maybe threadedly engaged with luer collar 40 at distal end 26 of barrel 22. Thus, lumen 20 through inserter needle 12 is placed in communication with lumen 48 through inner cannula 42. Assembly may be completed by slidably inserting guide wire 64 into small diameter guide wire aperture 60 in the proximal end of stopper 52. As noted above, the outside diameter of guide wire 64 is approximately equal to inside diameter "g" of guide wire aperture 60 in stopper 52, such that guide wire 64 effectively closes guide wire aperture 60 in stopper 52. Guide wire 64 may be retained in this position by frictional engagement in slit 62 adjacent distal end 56 of stopper 52.

Although the preferred embodiment of this invention includes a porous vent plug which is slidably mounted with the barrel, internally or externally, it is within the purview of the present invention to include a porous vent plug which is fixedly mounted in a fluid-tight engagement with the barrel so that the there is always fluid communication between the apertures through the inner cannula and the blood flashback chamber. Also, as mentioned hereinabove, it is also within the purview of the instant invention to include a plug or equivalent structure which is not made of air permeable, liquid impermeable material. The guide wire engaging the stopper and/or the interior of the inner cannula, depending on the dimensions chosen for these components, will prevent blood from leaving the proximal end of the cannula. By providing a movable vent plug in the preferred embodiment the invention has the additional feature of being able to safely contain the blood collected in the flashback chamber for containment and disposal even after the guide wire is removed from the device.

Apparatus 10 is employed as shown in FIG. 2 by inserting distal tip 14 of needle cannula 12 into a patient P. Upon accessing an artery A of patient P, pulsating blood B from artery A will flow through lumen 20 of inserter needle 12 and through lumen 48 of inner cannula 42. Blood from inner cannula 42 will exit apertures 50, and will pulsate into chamber 30 of barrel 22. Porous vent plug 70 permits air in chamber 30 to escape as blood B pulsate through apertures 50 of inner cannula 42. Thus, the pulsating blood flow into chamber 30 is not impeded by air pressure. However vent plug 70 functions to prevent escape of pulsating blood B. Guide wire 64 prevents the pulsating blood B from flowing completely through inner cannula 42 and exiting at proximal end 24 of apparatus 10. Thus, all of the pulsating blood B is safely contained in chamber 30 of barrel 22, and the cardiologist or radiologist employing apparatus 10 is substantially free of risk of exposure to contaminated blood.

Figure 7:
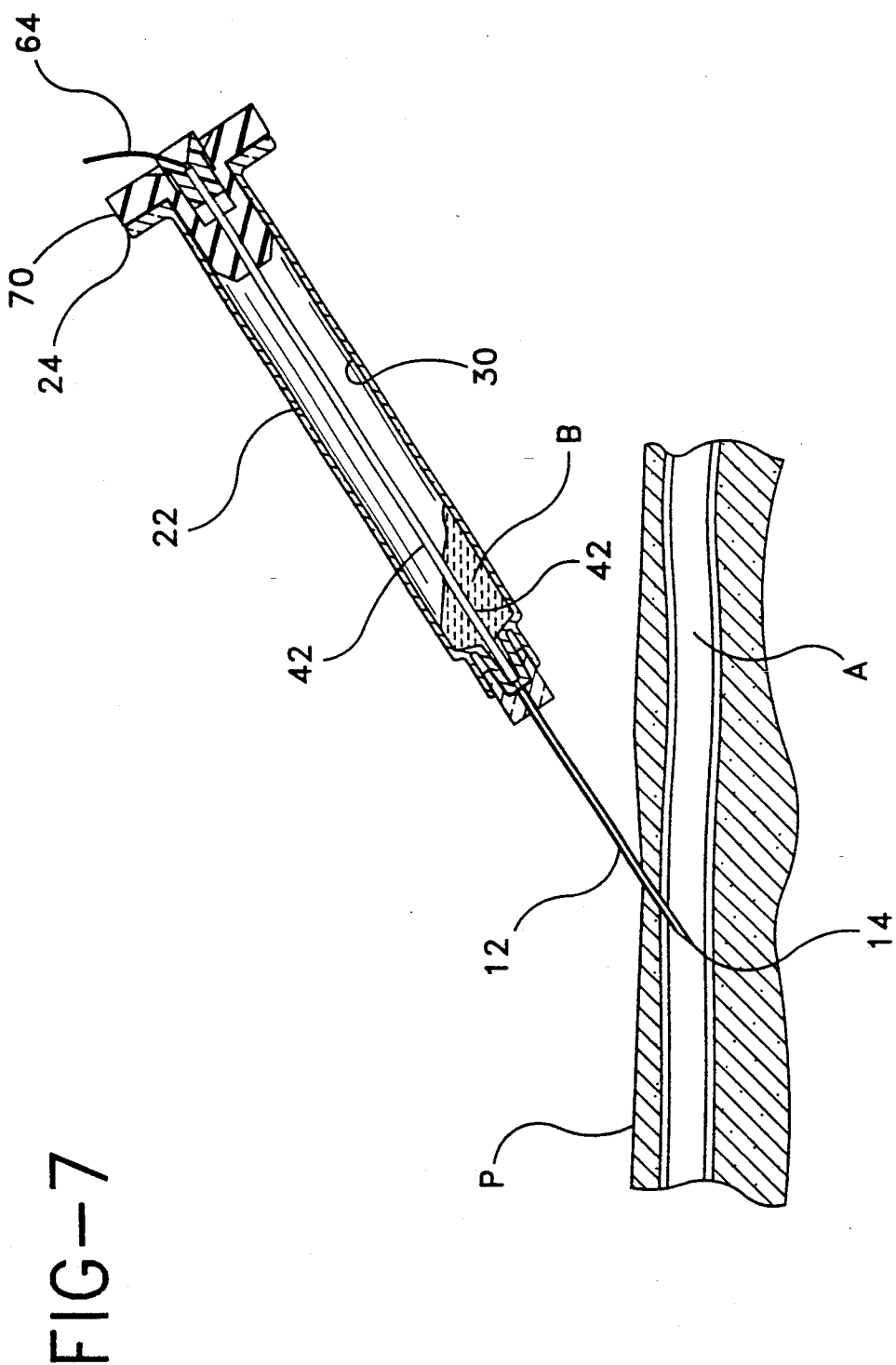
FIG. 7 is a cross-sectional view similar to FIG. 2 but showing the apparatus in a second operational condition.
Figure 8:
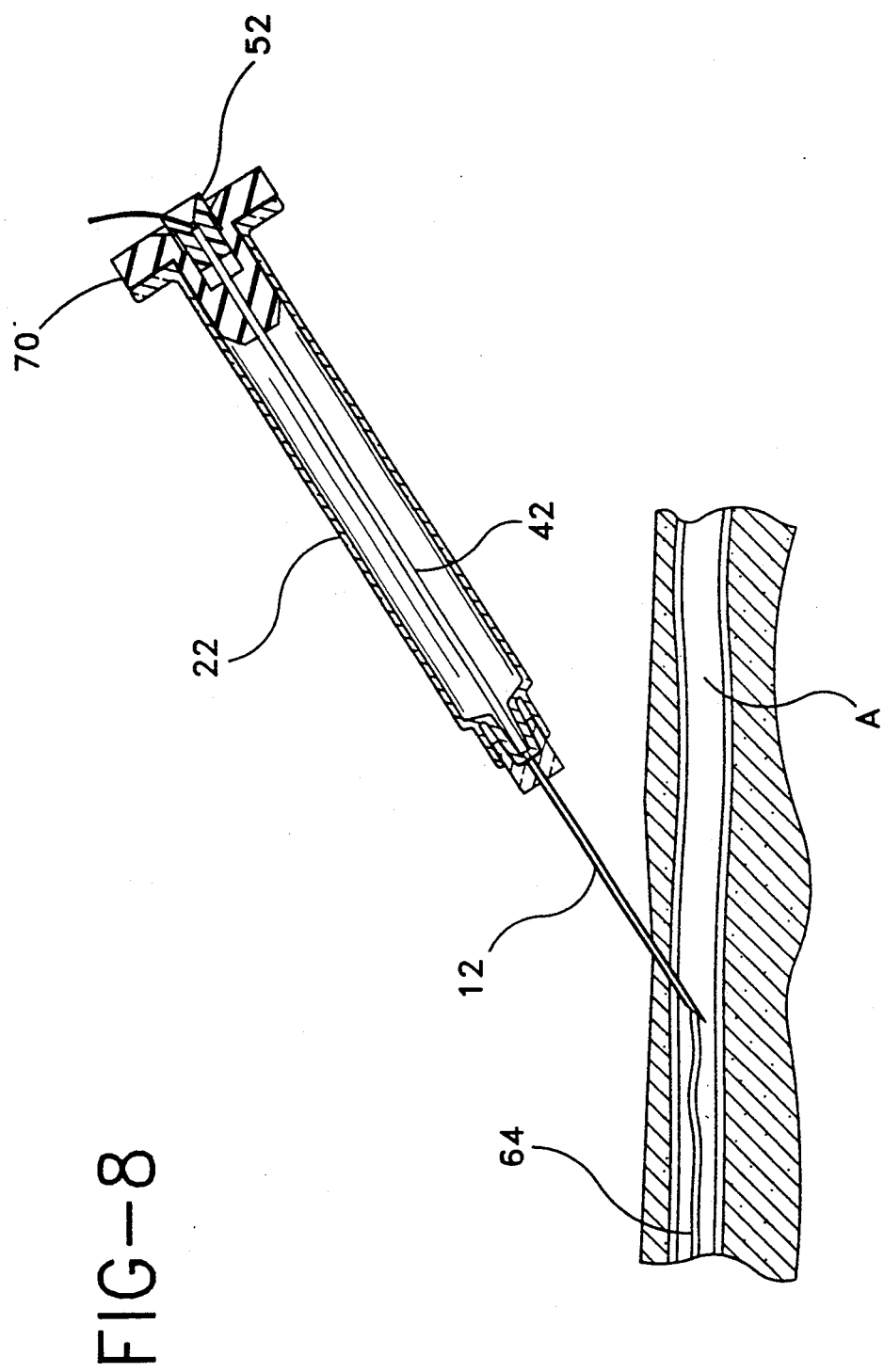
FIG. 8 is a cross-sectional view similar to FIGS. 2 and 7 but showing the apparatus in a third operational condition.
Figure 9:
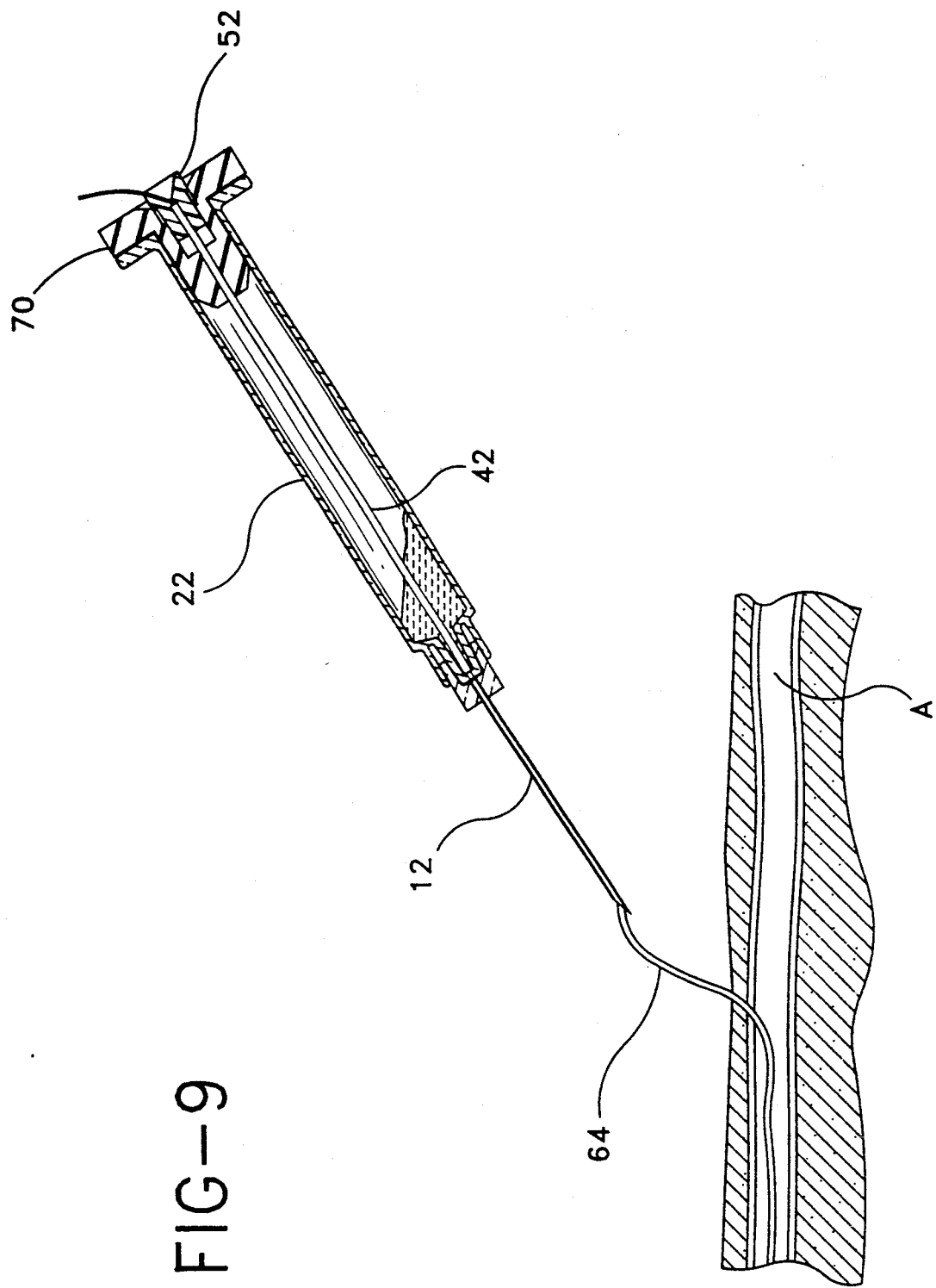
FIG. 9 is a cross-sectional view similar to FIGS. 2, 7 and 8 but showing the apparatus in a fourth operational condition.
Figure 10:
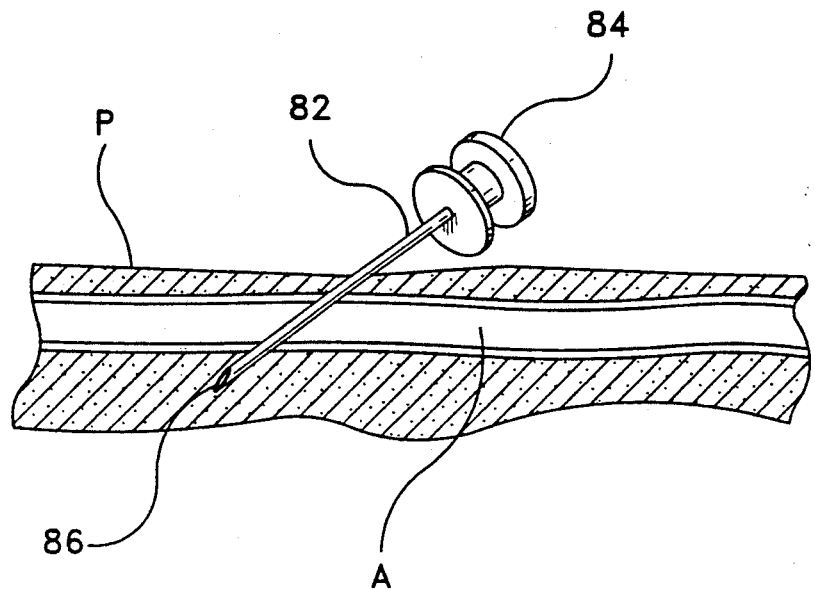
FIG. 10 is a cross-sectional view of an alternate inserter needle and stylet adapted for use with the apparatus of the subject invention and applicable for a double-walled puncture procedure.

The cardiologist or radiologist employing apparatus 10 can readily observe and identify the pulsating blood flow into chamber 30 which is indicative of access into an artery. Use of apparatus 10 proceeds by disengaging guide wire 64 from slit 62 in stopper 52., and advancing guide wire 64 longitudinally in a distal direction completely through inner cannula 42 and inserter needle 12 and into artery A of patient P, as shown in FIG. 8. Guide wire 64 is advanced sufficiently for the diagnostic procedure to be performed on patient P. The cardiologist or radiologist then slidably advances vent plug 70 in a distal direction to close apertures 50 in inner cannula 42, as shown in FIG. 7, thereby preventing further flow of blood. Flanges 25 on barrel 22 are provided to facilitate advancing the vent plug by providing a surface to apply digital pressure so that the user can urge the porous plug toward the distal end of the barrel. Remaining portions of apparatus 10 may then be removed by merely withdrawing inserter needle 12 from patient P and slidably moving apparatus 10 in a proximal direction relative to both patient P and guide wire 64.

It should be noted that the device of the instant invention can be used with an introducer needle which includes a catheter over its outside diameter. Accordingly, inserting the distal tip 14 of needle cannula 12 into the patient will also introduce the catheter into the patient. Upon making contact with the blood vessel and performing any necessary preliminary procedure, the device, including the introducer needle, may be removed leaving the catheter in the patient's vascular system for further therapeutic procedures.

Figure 11:
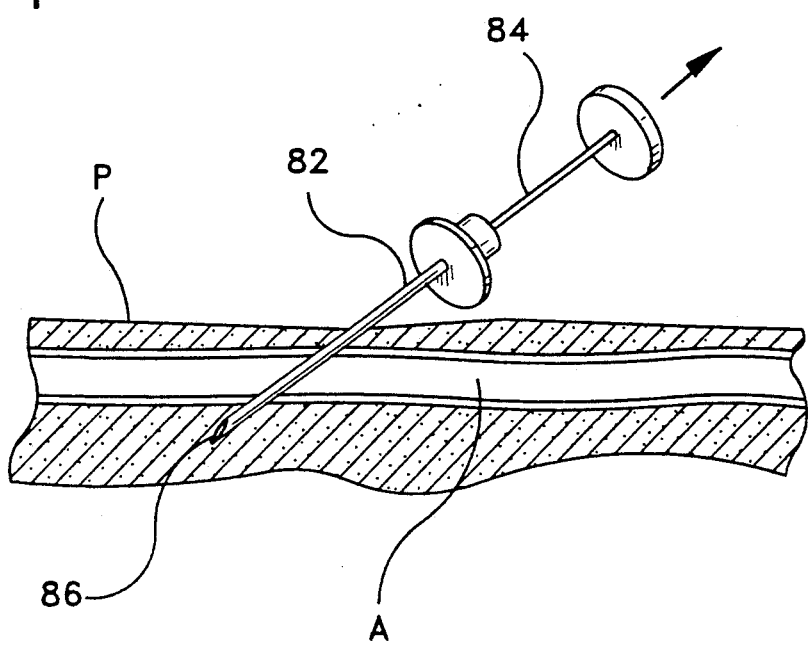
FIG. 11 is a cross-sectional view similar to FIG. 10, but showing a second operational condition of the alternate embodiment.

An alternate embodiment of the subject invention is illustrated in FIGS. 10-13 and is intended for cardiologists or radiologists who wish to access a blood vessel by employing a double-walled puncture technique. The alternate embodiment depicted in FIGS. 10-13 employs a barrel 22 with an inner cannula 42, a stopper 52, a guide wire 64 and a vent plug 70 substantially identical to those described and illustrated above. However, the embodiment depicted in FIGS. 10-12 starts with a separate inserter needle 82 with a stylet 84 slidably disposed therein. The combined needle 82 and stylet 84 are advanced entirely through an artery A of patient P, so that tip 86 of inserter needle 82 is beyond artery A. After completing this double puncture of two opposed arterial walls, stylet 84 is axially removed from the inserter needle in a proximal direction as shown in FIG. 11. The inserter needle 82 is then threadedly engaged with luer collar 40 of barrel 22, as shown in FIG. 12, such that inserter needle 82 communicates with inner cannula 42. Barrel 22 and inserter needle 82 are then moved proximally, as shown in FIG. 13, so that the tip 86 of needle 82 moves into artery A of patient P. This will cause pulsating blood B from artery A to be urged through inner cannula 42. Blood B will pass through aperture 50 of inner cannula 42 and can be visibly observed entering chamber 30 of barrel 22. Porous vent plug 70 may then be advanced distally and guide wire 68 may be fed into artery A substantially as described above.

While the invention has been described with respect to preferred embodiments, it is apparent that various changes can be made without departing from the scope of the invention as defined by the appended claims. For example, the apparatus may be used for inserting a guide wire into a vein. Although the flow of blood from a vein into the chamber of the apparatus will differ from the pulsating blood flow for an arterial access, a safe and readily identifiable venous blood flow can be observed.

What is claimed is:

1. A blood flashback containment apparatus comprising:
    a barrel having opposed proximal and distal ends and a chamber therebetween, said distal end of said barrel having a distal opening;
    an inner cannula mounted in said chamber, said inner cannula having a distal end communicating with said distal opening of said barrel, a proximal end and a lumen extending therebetween, said inner cannula including at least one aperture extending through said inner cannula providing communication between said lumen and said chamber;
    means for preventing blood flow out of said proximal end of said inner cannula; and
    a porous vent plug disposed in said chamber in sliding fluid-tight engagement with both said barrel and said inner cannula, said porous vent plug being slidably movable from a proximal position where said aperture through said inner cannula is exposed, to a distal position where said porous vent plug covers said aperture through said inner cannula, whereby blood flashback is contained and visually observable in said blood-receiving chamber of said barrel when said porous vent plug is in said proximal position, and whereby blood flashback is terminated when said porous vent plug is advanced to said distal position.

2. An apparatus as in claim 1 further including a guide wire positioned in and being movable through said inner cannula.

3. An apparatus as in claim 2 wherein said means for preventing blood flow out of said proximal end of said inner cannula includes said guide wire being dimensioned and disposed for preventing fluid flow through said lumen of said inner cannula between said aperture and said proximal end of said inner cannula.

4. An apparatus as in claim 2, further comprising a stopper having a passageway therethrough and mounted in fluid-tight engagement around said proximal end of said inner cannula.

5. An apparatus as in claim 4, further comprising means for releasably holding said guide wire.

6. An apparatus as in claim 5, wherein said means for holding said guide wire comprises a slit in said stopper for frictionally retaining said guide wire therein.

7. An apparatus as in claim 4 wherein said means for preventing blood flow out of said proximal end of said inner cannula includes a portion of said passageway of said stopper being sized to contact said guide wire to prevent blood flow past said portion of said passageway.

8. An apparatus as in claim 1, wherein said porous vent plug includes a flange disposed externally of said barrel and dimensioned for limiting said movement of said vent plug in said chamber.

9. An apparatus as in claim 1 further comprising an inserter needle removably engaged with said distal end of said barrel for communication with said inner cannula.

10. A blood flashback containment apparatus comprising:
    a barrel having an open proximal end, a distal end and a chamber wall extending therebetween and defining a flashback chamber, a distal opening extending through said distal end of said barrel;
    an inner cannula having opposed proximal and distal ends and a lumen extending therebetween, said distal end of said inner cannula being secured in said chamber for communication with said distal opening, at least one flashback aperture extending through said inner cannula at a location in said flashback chamber of said barrel;
    a stopper having opposed proximal and distal ends and an aperture extending therebetween, said proximal end of said inner cannula being securely engaged in said aperture of said stopper, said proximal end of said stopper including a slit formed therein;
    a guide wire slidably disposed in said aperture of said stopper and said slit being shaped to releasably retain said guide wire to help prevent axial motion of the guide wire with respect to said inner cannula, said guide wire being dimensioned to block fluid flow through said aperture of said stopper; and a porous vent plug formed from a gas transmissible liquid impervious material, said vent plug being slidably disposed in fluid-tight engagement within said barrel and slidably disposed in fluid-tight engagement around said inner cannula, said vent plug being slidable from a proximal position where said aperture in said inner cannula is exposed, to a distal position where said vent plug blocks said aperture in said inner cannula, whereby blood flowing into said inner cannula is prevented from leaving the proximal end of the inner cannula by the guide wire positioned in the stopper aperture and is permitted to flow into said flashback chamber when said vent plug is in said proximal position to provide a safe indication of access to a blood vessel.

11. A blood flashback containment apparatus comprising:

a barrel having an open proximal end, a distal end and a chamber therebetween, said distal end of said barrel having a distal opening;

an inner cannula mounted in said chamber, said inner cannula having a distal end communicating with said distal opening of said barrel, a proximal end and a lumen extending therebetween, said inner cannula including at least one aperture extending through said inner cannula providing communication between said lumen and said chamber;

a plug disposed in fluid-tight engagement with said proximal end of said barrel and said cannula, said cannula passing through said plug allowing access to said cannula by a guide wire inserted from the proximal end of said cannula; and vent means, communicating between said chamber and the exterior of said barrel for allowing air to leave said chamber as blood enters said chamber through said aperture in said cannula.

12. An apparatus as in claim 11 wherein said vent means includes said plug being at least partially made of air permeable, liquid impermeable material.

13. An apparatus as in claim 11 wherein said plug is in sliding engagement with said barrel and in sliding fluid-tight engagement around said inner cannula, said plug being slidable from a proximal position where said aperture in said inner cannula is exposed, to a distal position where said aperture in said inner cannula is covered by said plug.

14. An apparatus as in claim 11 further comprising an inserter needle mounted to said barrel and communicating with said inner cannula.

15. An apparatus as in claim 13, wherein said plug is slidably disposed in fluid-tight engagement within said chamber of said barrel.

16. An apparatus as in claim 11, further including means for releasably engaging said guide wire for preventing axial movement of said guide wire with respect to said inner cannula.

17. An apparatus as in claim 13, wherein said inner cannula further includes a stopper having opposed proximal and distal ends and an aperture extending therebetween securely mounted to said proximal end of said inner cannula, said lumen and said aperture being in fluid communication.

18. An apparatus as in claim 17, wherein said stopper includes means for releasably engaging said guide wire to help prevent axial motion of said guide wire with respect to said stopper.

19. An apparatus as in claim 11 further including means for preventing blood flow out of said proximal end of said inner cannula.

20. An apparatus as in claim 19 further including a guide wire positioned within and movable through said inner cannula.

21. An apparatus as in claim 20 wherein said means for preventing blood flow out of said proximal end of said inner cannula includes said guide wire being dimensioned and disposed for preventing fluid flow through said lumen of said inner cannula between said aperture and said proximal end of said inner cannula.

22. An apparatus as in claim 17 further including a guide wire positioned within and movable through said inner cannula and wherein said means for preventing blood flow out of said proximal end of said inner cannula includes a portion of said passageway of said stopper being sized to contact said guide wire to prevent blood flow past said portion of said passageway.

23. A method for safely inserting a guide wire into a blood vessel, said method comprising the steps of providing a barrel with a chamber and an inner cannula having a lumen therethrough, and said cannula having at least one aperture allowing fluid communication between said lumen and said chamber, an air-permeable, liquid-impermeable porous vent plug disposed sliding fluid-tight engagement in said barrel and in sliding fluid-tight engagement around said inner cannula; and placing said inner cannula in communication with said blood vessel, such that blood from said blood vessel passes through said lumen, through said aperture in said inner cannula and into said blood receiving chamber; while air in said chamber passes out of the chamber through said porous vent plug.

24. A method as in claim 23 further comprising the step of advancing said guide wire distally through said inner cannula and into said blood flow.

25. A method as in claim 24 further comprising the step of moving said vent plug relative to said inner cannula to block said aperture of said inner cannula and terminate said blood flow.

26. A method as in claim 23, wherein said barrel further includes an inserter needle mounted thereto, said inserter needle having a lumen communicating with said lumen of said inner cannula, and wherein said method of placing said inner cannula in communicating with said blood vessel comprises urging said inserter needle into said blood vessel.

* * * * *